(12) United States Patent
Dace et al.

(10) Patent No.: US 7,293,364 B2
(45) Date of Patent: Nov. 13, 2007

(54) MEASUREMENT DEVICE

(75) Inventors: Mark Dace, Collierville, TN (US); Bret Wilfong, Southaven, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 39 days.

(21) Appl. No.: 11/397,465

(22) Filed: Apr. 4, 2006

(65) Prior Publication Data

US 2007/0227023 A1    Oct. 4, 2007

(51) Int. Cl.
*A61B 5/103* (2006.01)
*G01B 3/28* (2006.01)

(52) U.S. Cl. .......................... 33/512; 33/836; 600/594

(58) Field of Classification Search ................. 33/512, 33/832, 833, 836; 600/587, 594
See application file for complete search history.

(56) References Cited

U.S. PATENT DOCUMENTS

| | | | |
|---|---|---|---|
| 3,559,292 A * | 2/1971 | Weissman | ................... 33/836 |
| 4,005,527 A | 2/1977 | Wilson et al. | |
| 4,033,043 A | 7/1977 | Cunningham | |
| 4,779,349 A * | 10/1988 | Odensten et al. | ............. 33/512 |
| 5,013,318 A | 5/1991 | Spranza, III | |
| 5,082,003 A * | 1/1992 | Lamb et al. | ................... 33/512 |
| 5,208,845 A | 5/1993 | Gelb | |
| 5,836,937 A | 11/1998 | Holmes | |
| 6,145,509 A | 11/2000 | Tanner | |
| 7,165,336 B2 | 1/2007 | Kim | |
| 7,179,262 B2 | 2/2007 | Bryan et al. | |
| 2006/0107118 A1 | 5/2006 | Alperin et al. | |
| 2006/0107119 A1 | 5/2006 | Kim et al. | |
| 2006/0207119 A1 * | 9/2006 | Kim et al. | ................... 33/512 |
| 2006/0276800 A1 | 12/2006 | Lee et al. | |
| 2007/0088364 A1 | 4/2007 | Ruhling et al. | |
| 2007/0088365 A1 | 4/2007 | Ruhling et al. | |

* cited by examiner

*Primary Examiner*—G. Bradley Bennett
(74) *Attorney, Agent, or Firm*—Haynes and Boone, LLP (57) ABSTRACT

A measurement device to determining a length of an anatomical feature is provided. In one embodiment, the measurement device is a depth gauge adapted to measure the depth of a vertebral endplate. The depth gauge may includes a probe that travels into the disc space. The depth gauge also includes a cam dial for indicating measurements.

28 Claims, 5 Drawing Sheets

MEASUREMENT DEVICE

TECHNICAL FIELD

Embodiments of the present disclosure relate generally to devices and methods for accomplishing spinal surgery, and more particularly in some embodiments, to depth gauge devices capable of measuring lengths of vertebral bodies.

BACKGROUND

To date, the standard methods and instruments have not adequately addressed the need for devices, systems, and procedures that accurately assess lengths of anatomical features in a simple manner. Accordingly, there is a need for improved depth gauge devices that avoid the drawbacks and disadvantages of the known devices and techniques.

SUMMARY

In one embodiment, a measurement device for measuring anatomical features is provided.

In another embodiment, a measurement device for measuring a length of a vertebra is provided. The measurement device includes a body having a proximal portion, a distal portion, a longitudinal axis extending between the proximal portion and the distal portion, and a passageway extending along the longitudinal axis from the proximal portion to the distal portion. The device also includes an engagement mechanism adapted to position the body in a position with respect to the vertebra. Further a probe is adapted to travel at least partially within the passageway of the body and along the longitudinal axis. The probe includes an indicator. A locking member is adapted to secure the probe in a fixed position with respect to the body. Finally, the measurement device includes a cam dial for indicating the length of the vertebra. The cam dial has an increasing radius and is configured such that the cam dial may be rotated until an outer surface of the cam dial—defined by the increasing radius—touches the indicator of the probe.

In another embodiment a method for measuring a length of a vertebra is provided. The method includes providing a depth gauge having a body portion, an extendable probe portion, and a cam dial. The extendable probe portion including a distal tip and an indicator. The cam dial has an increasing radius and an outer surface defined by the increasing radius. The method also includes securing the depth gauge into a fixed position relative to the vertebra; extending the probe portion until the distal tip reaches a boundary of the vertebra; locking the probe portion into position relative to the body of the depth gauge; and rotating the cam dial until the outer surface touches the indicator to indicate a measurement of the length of the vertebra.

Additional and alternative features, advantages, uses, and embodiments are set forth in or will be apparent from the following description, drawings, and claims.

DESCRIPTION

The present disclosure relates generally to measurement devices, and more particularly, to depth gauges for measuring features of vertebrae. For the purposes of promoting an understanding of the principles of the invention, reference will now be made to the embodiments, or examples, illustrated in the drawings and specific language will be used to describe the embodiments. It will nevertheless be understood that no limitation of the scope of the invention is intended. Any alterations and further modifications of the described embodiments, and any further applications of the principles of the invention as described herein are contemplated as would normally occur to one skilled in the art to which the invention relates.

Figure 1:
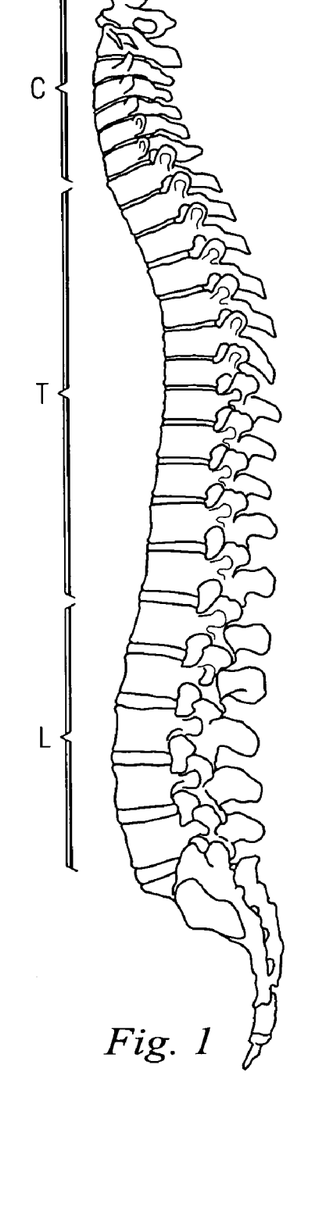
FIG. 1 is a sagittal view of a human spine.

FIG. 1 is a sagittal view of a human spine showing the various regions of the spine: cervical C, thoracic T, and lumbar L. Often in spine surgery it is necessary to accurately measure aspects of the vertebrae, such as vertebral endplate length and vertebral body height. For example, the dimensions of a vertebra may be used to determine the appropriate size of an implant that will be used in conjunction with the vertebra. The functionality of the implant may be impaired if not sized correctly. For this and other reasons, it is important that the measurements are accurate and precise. As described in detail below, the embodiments of the present disclosure facilitate accurate and precise measurement of vertebrae as may be necessary in spine surgery.

Figure 2:
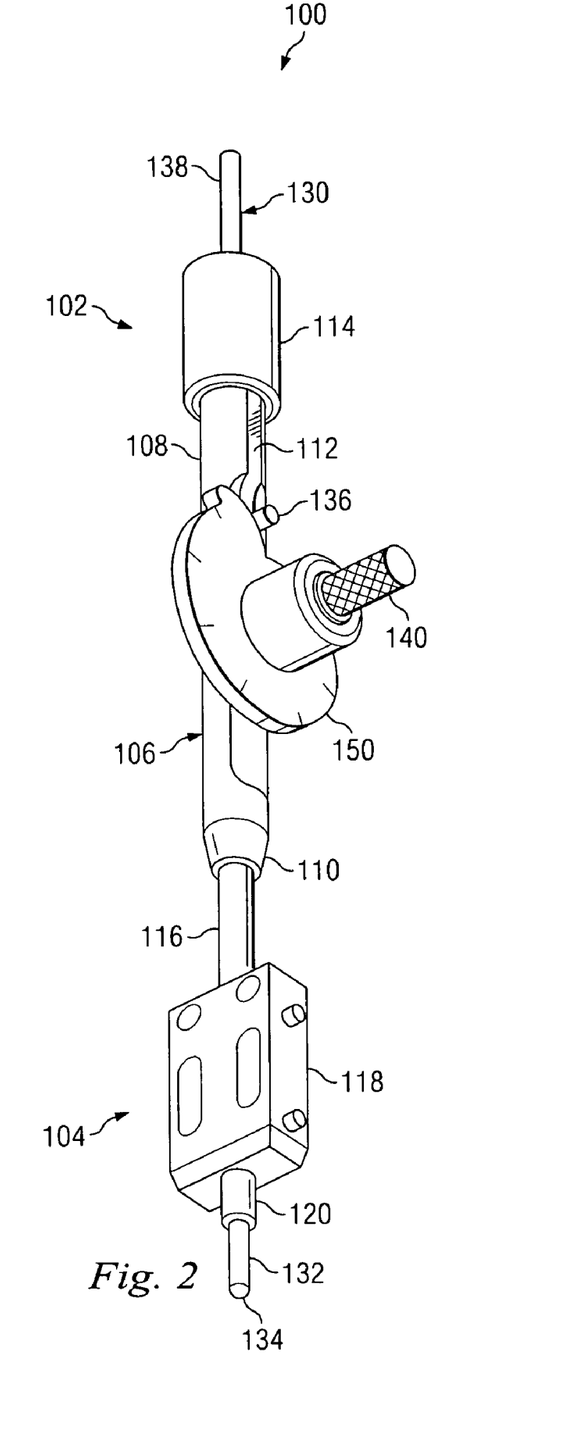
FIG. 2 is a perspective view of a depth gauge according to one embodiment of the present invention.

Referring now to FIG. 2, shown therein is a perspective view of a measurement device according to one embodiment of the present invention. The depth gauge 100 has a proximal portion 102 and a working or distal portion 104. The depth gauge 100 includes a main body 106, a gripping portion 114, an engagement portion 118, a probe 130, a locking member 140, and a cam dial 150. The main body 106, the gripping portion 114, a body extension 116, and the engagement portion 118 include a hollow passage adapted to allow the probe 130 to travel along a longitudinal axis L of the depth gauge 100.

The main body 106 includes an upper portion 108, a lower portion 110, and channel 112. The channel 112 is adapted to provide a path for an indicator 136 of the probe 130 to travel. In some embodiments, the channel 112 is bounded by the gripping portion 114 as it extends towards the proximal portion 102 of the depth gauge 100 such that the indicator 136 cannot travel proximally beyond the bottom of the gripping portion. Also, in some embodiments the channel 112 is bounded by the cam dial 150 as it extends towards the distal portion 104 of the depth gauge 100 such that the indicator 136 cannot travel distally beyond the cam dial. In other embodiments, the channel 112 includes its own boundaries formed in the main body 106. Channel 112 is adapted to correspond to the lengths measured by the depth gauge 100. That is to say, if the depth gauge 100 is adapted to measure lengths between 12 mm and 20 mm, as shown on cam dial 150 in FIG. 2, then the channel 112 should allow the indicator 136 to travel 8 mm—the difference between 20 mm and 12 mm. The depth gauge 100 may be scaled to measure lengths of any size. However, the depth gauge 100 is especially adapted for measuring lengths between 0.01 mm and 100 mm, and more particularly lengths between 8 mm and 24 mm.

In some embodiments the upper portion 108 is adapted to engage the gripping portion 114. For example, the upper portion 108 and the gripping portion 114 may be threaded such that they mate with one another. Similarly, the upper portion 108 may include a projection adapted to engage a recess of the gripping portion 114, or vice-versa. In other embodiments, the upper portion 108 and the gripping portion 114 are formed as a single piece and, therefore, do not engage each other as they are a single piece. Also, in some embodiments the lower portion 110 is adapted to engage body extension 116. Similar to the upper portion 108 and the gripping portion 114, the lower portion 110 and the body extension 116 may engage one another or be formed as a single piece.

The gripping portion 114 is adapted to be grasped by a user or another instrument. To this end, the gripping portion 114 may include a textured surface. For example, the surface may be roughened by chemical etching, bead-blasting, sanding, grinding, serrating, or diamond-cutting. Similarly, the gripping portion 114 may include recesses, protrusions, threads, or other features to facilitate engagement by another instrument. In some embodiments, the gripping portion 114 is configured such that the depth gauge 100 may be held in one hand by the user.

The body extension 116 extends from the lower portion 110 of the main body 106 towards working portion 104. The body extension 116 includes or is connected to engagement portion 118. In some embodiments, the body extension 116 and the engagement portion 118 are formed as a single unit. In other embodiments, the engagement portion 118 is configured to engage the body extension 116 in some manner. The means of engagement between the engagement portion 118 and the body extension 116 may be of any type that will secure the engagement portion to the body extension.

Figure 6:
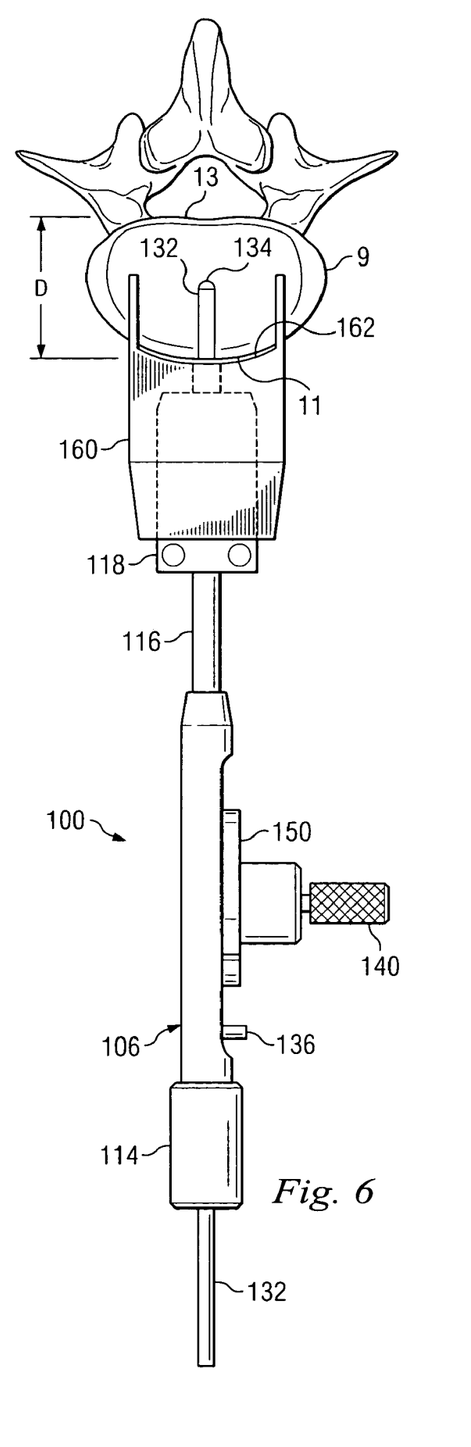
FIG. 6 is a top view of a depth gauge according to one embodiment of the present invention in combination with a milling block measuring the depth of a vertebral endplate.
Figure 7:
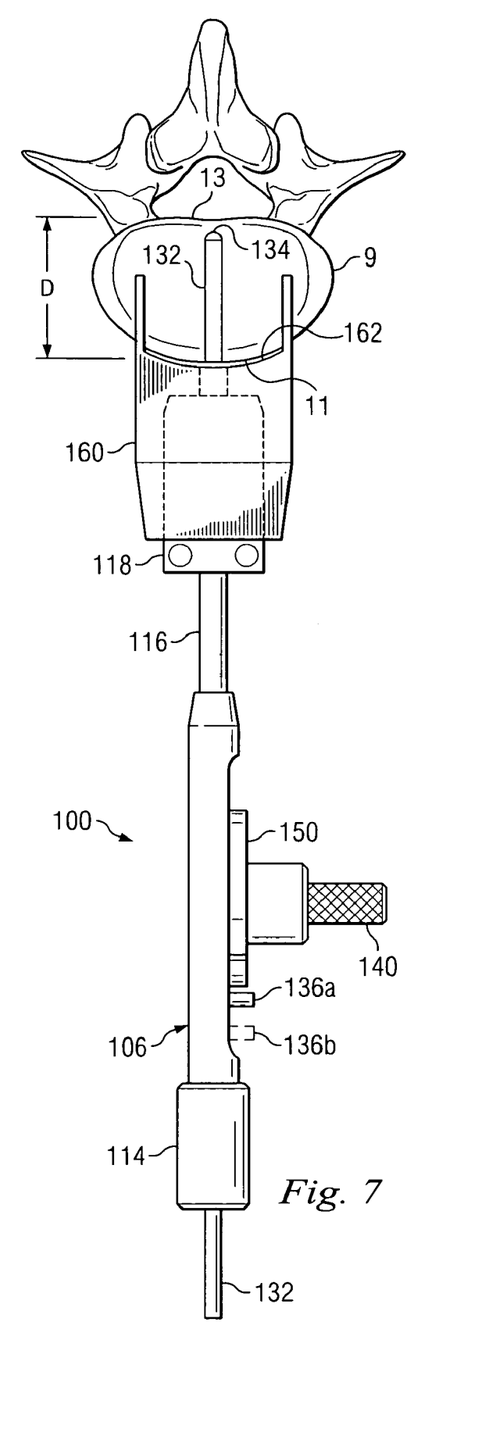
FIG. 7 is a top view of a depth gauge according to one embodiment of the present invention in combination with a milling block measuring the depth of a vertebral endplate.
Figure 8:
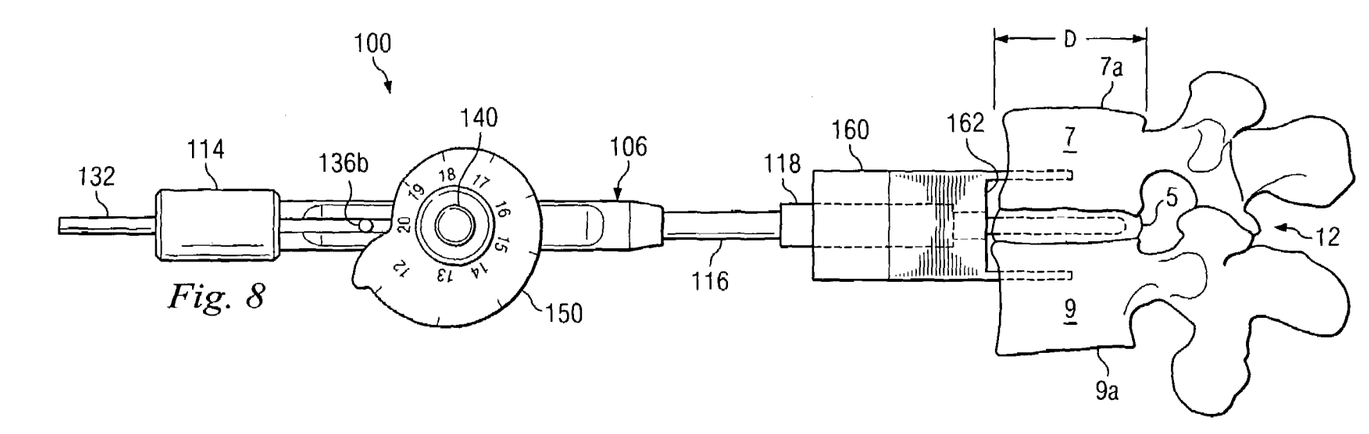
FIG. 8 is a side view of the depth gauge in combination with a milling block measuring the depth of a vertebral endplate of FIG. 7.

The engagement portion 118 is configured to secure the depth gauge 100 in place with respect to a superior vertebra 7 and an inferior vertebra 9. As shown in FIGS. 6-8, in some embodiments the engagement portion 118 is adapted to engage a milling block 160 or other similar device. In such embodiments, the milling block 160 is secured to or driven into vertebrae 7, 9 to create an opening to the disc space. In one embodiment, the milling block is secured to the vertebrae 7, 9 using screws. The engagement portion 118 is then connected to or otherwise engaged to the milling block 160. For example, in some embodiments the engagement portion 118 slides into an opening of the milling block 160 such that protrusions of the milling block engage recesses of the engagement portion securing the engagement portion to the milling block. In this way, the depth gauge 100 is locked into position. In some embodiments the engagement portion 118 selectively engages the milling block 160 such that the depth gauge may be removed without removing the milling block. In other embodiments the engagement portion 118 is adapted to engage the vertebrae 7,9 directly and, thereby, secure the location of the depth gauge 100 with respect to the vertebrae.

Whether the engagement portion 118 is adapted to engage the milling block 160 or the vertebrae 7,9, the engagement portion orients the depth gauge 100 relative to a reference point. In some embodiments the reference point is an anterior edge 11 of the vertebra 9. For example and as shown in FIGS. 6-8, where the engagement portion 118 is adapted to engage the milling block 160, an exterior surface 162 of the milling block abuts the anterior edge 11 of the vertebra 9. The exterior surface 162 is adapted to substantially match the contour of the anterior edge 11 of the vertebra 9. The manner of engagement between the engagement portion 118 and the milling block 160 is such that the orientation of the depth gauge 100 with respect to the exterior surface 162 of the milling block and, therefore, the anterior edge 11 of vertebra 9, is known. Thus, when the engagement portion 118 engages the milling block 160, the depth gauge 100 is oriented with respect to the anterior edge 11 of the vertebra 9 at a known distance. This provides the depth gauge 100 with a reference point from which length can be accurately measured. The engagement portion 118 itself may serve to provide a similar reference point where the engagement portion is adapted to engage the vertebrae 7, 9 directly. Again, in some embodiments the reference point is the anterior edge of one of the vertebrae 7, 9.

In some embodiments a tube portion 120 is part of the body extension 116 and passes through at least a portion of engagement portion 118. In other embodiments, the tube portion 120 is part of the engagement portion 118. In some embodiments, the tube portion 120 is sized such that when the depth gauge 100 is secured with respect to the vertebrae 7, 9 the distal end of the tube portion aligns with the anterior edge of one of the vertebrae. Thus, a distal tip 134 of the probe 130 may extend into the disc space beginning from the anterior edge of the vertebrae. In some embodiments this facilitates accurate measurement of the length of the vertebral endplate by allowing measurement from the anterior edge 11 of the vertebra 9 to a posterior edge 13 of the vertebra 9. In other embodiments, the tube portion 120 is sized such that it extends at least partially into the disc space when the depth gauge 100 is secured with respect to the vertebrae 7, 9. In yet another embodiment, the depth gauge 100 does not include tube portion 120.

Figure 4:
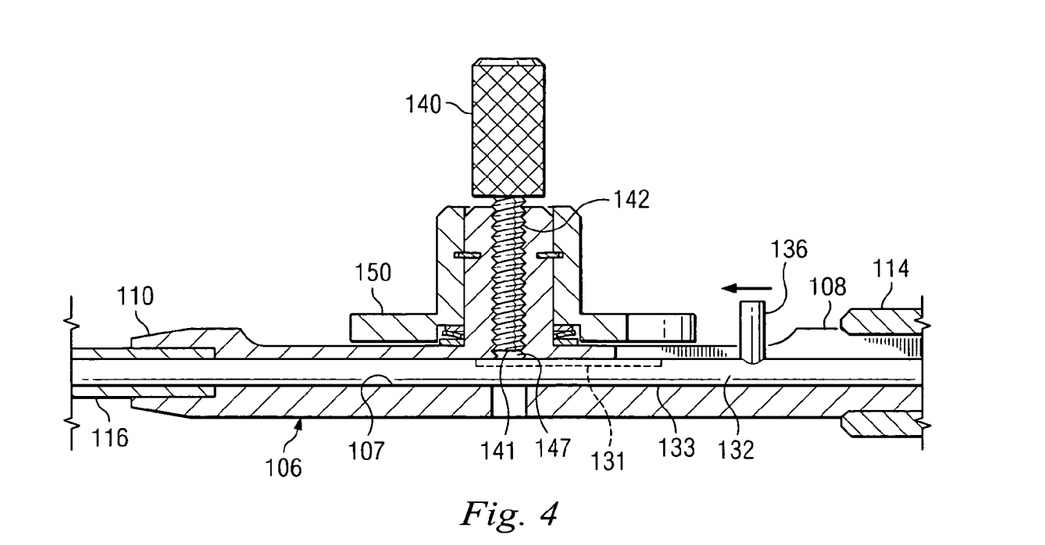
FIG. 4 is a partial, cross-sectional view of the depth gauge of FIG. 2 where the locking pin is not engaging the probe shaft.
Figure 5:
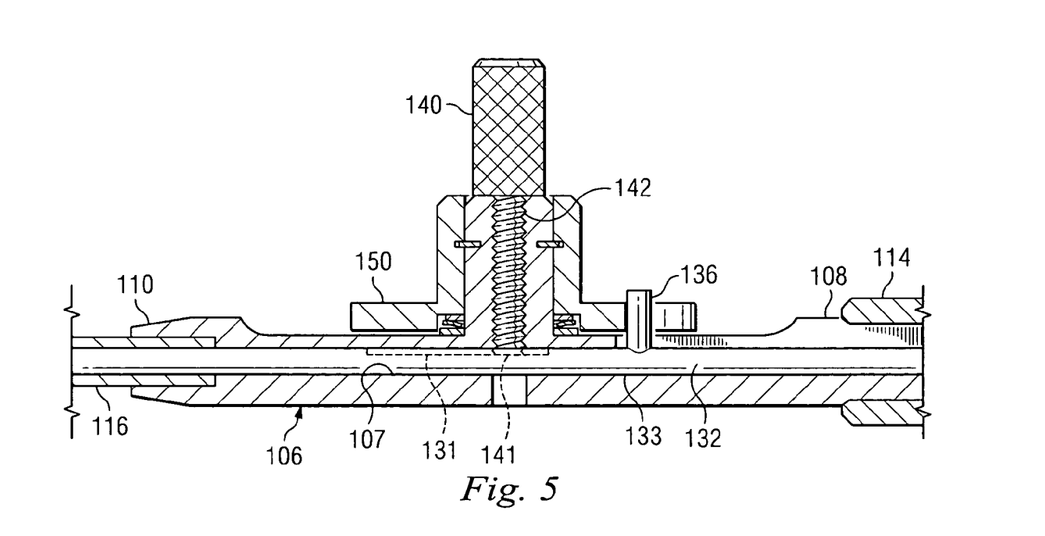
FIG. 5 is a partial, cross-sectional view of the depth gauge of FIG. 2 where the locking pin is securing the probe shaft in place.

The probe 130 is adapted to translate along the longitudinal axis L of the depth gauge 100. The probe 130 includes a probe shaft 132, the distal tip 134, an indicator 136, and a proximal portion 138. The probe shaft 132 is sized such that it may pass through openings or passages in the other components of the depth gauge 100. FIGS. 4 and 5 illustrate the relationship between the probe shaft 132 and the main body 106, gripping portion 114, and body extension 116. As shown in FIGS. 4 and 5, in some embodiments there is a gap between the probe shaft 132 and the inner walls of the these components. However, in other embodiments the probe shaft 132 and the other components are sized such that there is virtually no gap between the probe shaft and the inner walls—there is only sufficient room to allow the probe to travel along the longitudinal axis L of the depth gauge 100.

The distal tip 134 is adapted to be distinguishable when viewed through various imaging techniques. For example, in some embodiments the distal tip 134 is treated to be radio-opaque such that it is easily distinguishable in fluoroscopy images. Where the depth gauge 100 is utilized to measure the length of a vertebral endplate, the probe 130 may be extended into the disc space until the distal tip 134 reaches a posterior edge of the endplate. In some embodiments, fluoroscopy is used to determine when the distal tip 134 reaches the posterior edge of the vertebral endplate. Similarly, the distal tip 134 may be treated to be distinguishable under other imaging techniques such as computed tomography, ultrasound, or magnetic resonance imaging. Further, as shown in FIG. 2 the distal tip 134 may have a greater width than the rest of the probe shaft 132 to help distinguish the tip from the rest of the shaft when imaged. However, as shown in FIG. 3 the distal tip 134 has the same width as the rest of probe shaft 132 in some embodiments.

The indicator 136 is adapted to be used as a reference marker for determining how far the probe 130 has traveled. As shown in FIGS. 2-10, the indicator 136 may be a pin or other protrusion that extends from the probe shaft 132. However, it is not necessary for the indicator 136 to protrude from the probe shaft 132. For example, the indicator could simply be a viewable marking on the probe shaft 132 such as a colored line, laser etching, or the like. As will be described in greater detail below, the indicator need only provide a reference point from which the cam dial 150 may be used to determine the length traveled by the probe 130. Thus, the indicator 136 may be located anywhere upon the probe shaft 132 as long as it is accessible by the cam dial 150 for determining measurements.

The proximal portion 138 of the probe 130 is adapted to be gripped by the user so that the user may extend and retract the probe. To this end, in some embodiments the proximal portion is textured or otherwise treated to facilitate gripping of the probe. Further, in some embodiments the proximal portion 138 is adapted to be engaged by another instrument and includes an attachment means to facilitate such a connection.

Figure 3:
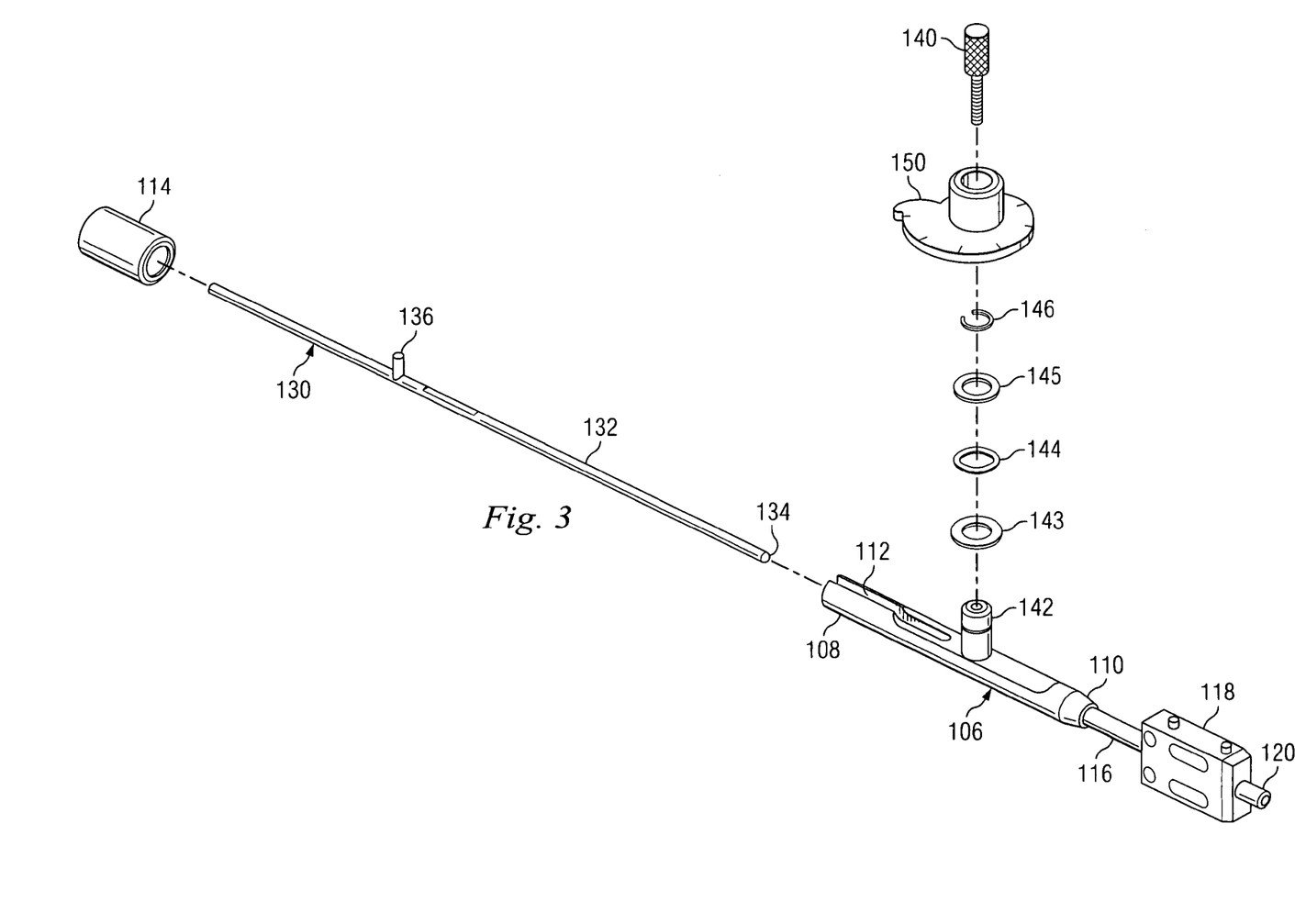
FIG. 3 is an exploded view of the components of the depth gauge of FIG. 2.

As shown in FIG. 3, the locking member 140 and the cam dial 150 are connected to the main body 106 via post 142 protruding from the main body. Also as shown in FIG. 3, the means of connecting the locking member 140 and the cam dial 150 to the main body 106 may include a first washer 143, a wave spring 144, a second washer 145, and a retaining ring 146. These components are, however, not necessary in other embodiments and are shown merely for exemplary purposes. The locking member 140 and the cam dial 150 may be connected to the main body 106 using any reasonable means.

As shown most clearly in FIGS. 4 and 5, locking member 140 is adapted to secure the probe 130 in a fixed position relative to the other components of the depth gauge 100. The locking member 140 may include any means for holding the probe 130 in a locked position. For example, the locking member 140 may be a screw, a pin, magnet, or other devices. As shown in FIGS. 4 and 5, in one embodiment the locking member 140 is a screw-type device. When not securing the probe 130 in place, there is a gap 147 between an engagement surface 141 of the locking member 140 and a first surface 131 of the probe shaft. When the locking member 140 is engaged the engagement surface 141 contacts the first surface 131 and causes a second surface 133 to contact an inner surface 107 of the main body 106. In this manner, the locking member 140 creates a friction lock between itself, the probe shaft 132, and the main body 106. In practice the locking member 140 allows the user to lock the probe 130 in place, which in turn allows the user to remove the depth gauge 100 from the disc space before using the cam dial 150 to determine a measurement.

In at least one embodiment, the depth gauge 100 includes a retraction mechanism adapted to retract the probe 130 to fixed position. Such a retraction mechanism is advantageous in that it prevents the inadvertent extension of the distal tip 134 of the probe 130 too far into the disc space. This can be of concern where the depth gauge 100 is aligned vertically such that proximal portion 102 is above the distal portion 104, which could allow the probe 130 to drop to its full extension if not controlled by the user. Thus, a retraction mechanism such as a spring or other device may be implemented to keep the probe 130 in a retracted position—towards the proximal portion 102 of the depth gauge 100—when not being extended by the user.

FIGS. 6-10 show one embodiment of a depth gauge 100 in use. Milling block 160 is secured to the vertebrae via prongs 164, 166. The depth gauge 100 is secured into position by engagement member 118 connecting to milling block 160. This provides the depth gauge 100 with a reference point to the anterior edge 11 of the vertebra 9. Once the depth gauge 100 is secured in place, the probe 130 is extended into the disc space as shown in FIG. 6. The probe 130 is extended into the disc space until the distal tip 134 reaches the posterior edge of the vertebra 9, as shown in FIGS. 7 and 8. The location of the distal tip 134 is monitored using an imaging technique such as fluoroscopy, as previously described.

Once the distal tip 134 reaches the posterior edge 11 of the vertebra 9, the probe 130 may be locked into position by locking member 140. As illustrated in FIG. 7, the indicator 136 travels from a first position 136a to a final position 136b as the probe 130 travels into the disc space. The final position 136b corresponds with the distal tip 134 reaching the posterior edge 11. Thus, when the locking member 140 secures the probe shaft 132 into position the indicator 136 will be secured into the final position 136b. FIG. 7 shows the locking member 140 in an engaged position securing the probe shaft 132 in place with respect to the main body 106. At this point the depth gauge 100 may be removed and the length of the vertebral endplate determined using cam dial 150.

Figure 9:
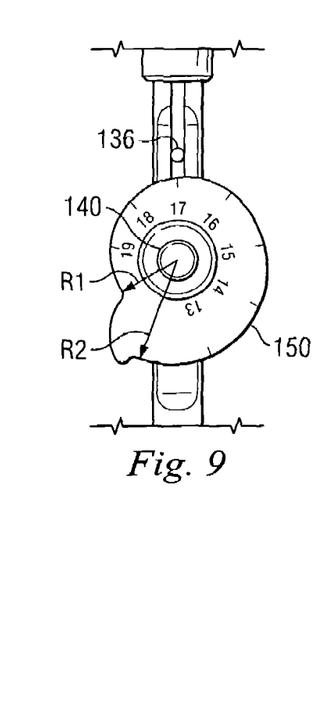
FIG. 9 is a perspective view of a cam according to one embodiment of the present invention.
Figure 10:
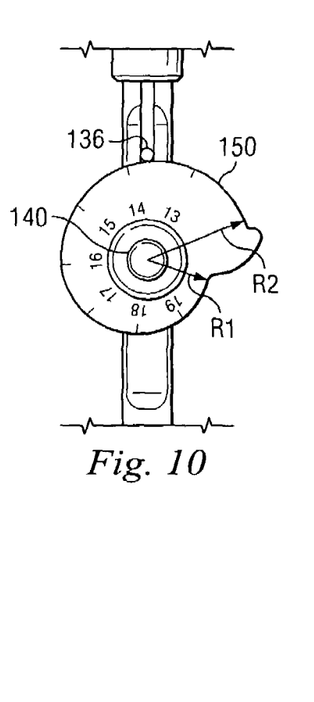
FIG. 10 is a perspective view of the cam of FIG. 9 rotated into a position to show a measurement reading.

FIGS. 9 and 10 illustrate how the cam dial 150 works. As shown, cam dial 150 has an increasing radius. In some embodiments the cam dial is configured such that a smaller radius corresponds to a greater length, as shown. However, in other embodiments—such as where the indicator 136 travels away from the cam dial 150 as the distal tip 134 extends into the disc space instead of towards the cam dial—a smaller radius corresponds to a smaller length. In either case the principle is the same—the increasing radius of the cam dial 150 corresponds to an equivalent change in length as measured by the travel of the probe 130. However, as described below, translating lengths around the circumference of the cam dial as increasing radii allows for more precise measurements.

The cam dial 150 is rotated until an edge of the cam dial touches the indicator 136 (or comes in line with the indicator where the indicator is not a protrusion). At that point, the measurement corresponding the distance measured by the probe is indicated. For example, the cam dial in FIG. 10 indicates a measurement of 15 mm because the edge of the cam dial is touching the indicator 136 at that measurement point. In some embodiments the measurements on the cam dial are subdivided to include more accurate measurements, such as tenths or hundredths of a millimeter.

The cam dial 150 is able to amplify the measurements by allowing the lengths to be translated around the circumference of the cam dial. This allows small differences in length to be distinguished more easily by spreading the differences in length over the entire circumference of the cam dial. Further, the cam dial 150 may be precise to different degrees such as the nearest mm, nearest tenth of a mm, nearest hundredth of a mm, and so on to allow further amplification of the measurements. In this regard, it is contemplated that multiple depth gauges may be utilized to obtain as accurate and precise a measurement as possible. For example, a first depth gauge that measures between 12 and 20 mm and precise to the nearest mm may be utilized to determine that the length is approximately 15 mm. Then a second depth gauge scaled to measure between 14 mm and 16 mm and precise to the nearest tenth of a mm may be utilized to determine a more accurate reading. Then a third depth gauge precise to the nearest hundredth of a mm may be used. This process may be iterated until the user is sufficiently satisfied with the accuracy and preciseness of the measurement.

In some embodiments the depth gauge 100 is made out of titanium, stainless steel, or other surgical grade materials. The cam dial 150 may be made of additional materials—such as plastics or polymers—so long as the material is dimensionally stable through an autoclaving cycle. In other embodiments, the depth gauge is disposable or adapted for a single use and therefore the materials do not need to survive an autoclave cycle and, preferably, would not survive an autoclave cycle.

The depth gauge 100 has been described primarily in relation to measuring the depth of a vertebral end plate. However, the depth gauge 100 is not limited to such applications. The features of the depth gauge 100—such as the cam dial size, the probe length, and the engagement mechanism—may be adapted or modified to measure most anatomical features. The concept of the present disclosure is applicable to all situations where an accurate and precise length measurement of anatomical feature is desired.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that all spatial references, such as "horizontal," "vertical," "top," "upper," "lower," "bottom," "left," and "right," are for illustrative purposes only and can be varied within the scope of the disclosure. In the claims, means-plus-function clauses are intended to cover the structures described herein as performing the recited function and not only structural equivalents, but also equivalent structures.

What is claimed is:

1. A measurement device for measuring a length of a vertebra, comprising:
    a body having a proximal portion, a distal portion, a longitudinal axis extending between the proximal portion and the distal portion, and a passageway extending along the longitudinal axis from the proximal portion to the distal portion;
    an engagement mechanism disposed adjacent the distal portion and adapted to position the body in a position with respect to the vertebra;
    a probe adapted to travel at least partially within the passageway of the body and along the longitudinal axis, the probe including an indicator;
    a locking member adapted to secure the probe in a fixed position with respect to the body; and
    a cam dial for indicating a movement of the probe, the cam dial having an increasing radius and configured such that the cam dial is rotatable until an outer surface of the cam dial defined by the increasing radius aligns with the indicator of the probe.

2. The measurement device of claim 1, wherein the movement of the probe indicates a depth of an endplate of the vertebra.

3. The measurement device of claim 1, wherein the body further includes a channel extending along the longitudinal axis and wherein the indicator of the probe is adapted to move within the channel.

4. The measurement device of claim 3, wherein the indicator is a protrusion extending from the probe.

5. The measurement device of claim 3, wherein the channel is further adapted to limit the travel of the probe to a defined range.

6. The measurement device of claim 5, wherein the defined range corresponds to a range of measurements that may be indicated by the cam dial.

7. The measurement device of claim 6, wherein the range of measurements is between about 0.1 mm and about 100 mm.

8. The measurement device of claim 1, wherein the engagement portion is adapted to selectively engage a milling block.

9. The measurement device of claim 1, wherein the engagement portion is adapted to engage the vertebra directly.

10. The measurement device of claim 1, wherein the body's position with respect to the vertebra is at an anterior edge of the vertebra.

11. The measurement device of claim 1, wherein the probe is adapted to be identified when viewed through an imaging technique.

12. The measurement device of claim 11, wherein the imaging technique is fluoroscopy.

13. The measurement device of claim 12, wherein at least a portion of the probe is radio-opaque.

14. The measurement device of claim 11, wherein a distal tip of the probe is adapted to be distinguishable from a main shaft of the probe.

15. The measurement device of claim 1, wherein the probe is biased towards the proximal portion of the body.

16. The measurement device of claim 1, wherein a portion of the probe is adapted to grasped by a user.

17. The measurement device of claim 16, wherein the portion of the probe adapted to be grasped by a user is textured.

18. The measurement device of claim 1, wherein the locking member is further adapted to secure the probe in a fixed position with respect to the body.

19. The measurement device of claim 18, wherein the locking member is adapted to secure the probe in the fixed position with respect to the body using friction.

20. The measurement device of claim 19, wherein the locking member is a screw.

21. A method for measuring a length of a vertebra, comprising:
    providing a depth gauge having a body portion, an extendable probe portion, and a cam dial; the extendable probe portion including a distal tip and an indicator; the cam dial having an increasing radius and an outer surface defined by the increasing radius;

securing the depth gauge into a fixed position relative to the vertebra;

extending the probe portion until the distal tip reaches a boundary of the vertebra;

locking the probe portion into position relative to the body of the depth gauge; and rotating the cam dial until the outer surface touches the indicator to indicate a measurement of the length of the vertebra.

22. The method of claim 21, further comprising releasing the depth gauge from the fixed position relative to the vertebra prior to the rotating of the cam dial.

23. The method of claim 21, further comprising monitoring the location of the distal tip of the probe via an imaging technique.

24. The method of claim 23, wherein the imaging technique is fluoroscopy.

25. The method of claim 21, wherein the length of the vertebra is a depth of the vertebral endplate.

26. The method of claim 25, wherein the depth gauge's fixed position relative to the vertebra is with respect to an anterior edge of the vertebra.

27. The method of claim 26, wherein the boundary of the vertebra is a posterior edge.

28. The method of claim 27, wherein the cam dial is adapted to indicate measurements in a range between 12 mm and 20 mm.

* * * * *